United States Patent [19]

Philpot, Jr.

[11] 4,012,502

[45] Mar. 15, 1977

[54] SNAKE VENOM INHIBITOR MATERIAL AND METHOD OF PURIFICATION

[76] Inventor: Van B. Philpot, Jr., P.O. Box 312, Houston, Miss. 38851

[22] Filed: Apr. 10, 1975

[21] Appl. No.: 566,995

Related U.S. Application Data

[63] Continuation-in-part of Ser. No. 399,469, Sept. 21, 1973, abandoned, which is a continuation of Ser. No. 239,327, March 29, 1972, abandoned.

[52] U.S. Cl. .................................. 424/98; 424/101
[51] Int. Cl.$^2$ ................ A61K 35/14; A61K 35/58
[58] Field of Search .............................. 424/101, 98

[56] References Cited

UNITED STATES PATENTS 3,504,083  3/1970  Philpot .............................. 424/101

*Primary Examiner*—Stanley J. Friedman
*Attorney, Agent, or Firm*—Cushman, Darby & Cushman

[57] ABSTRACT

A material extracted from snakes such as snake serum is purified to obtain an inhibitor for snake venom toxicity and/or proteolytic enzymes. Snake serum is treated to obtain a useful therapeutic agent present in the serum and attached to a high molecular weight protein molecule. The protein molecule is split and fragments thereof are removed along with unwanted antigenic protein material to thus separate a purified material having high inhibitor activity against snake venom toxicity and proteases. The resulting inhibitor material is relatively low in protein content with an increase of specific activity of many times that of crude serum.

8 Claims, 1 Drawing Figure

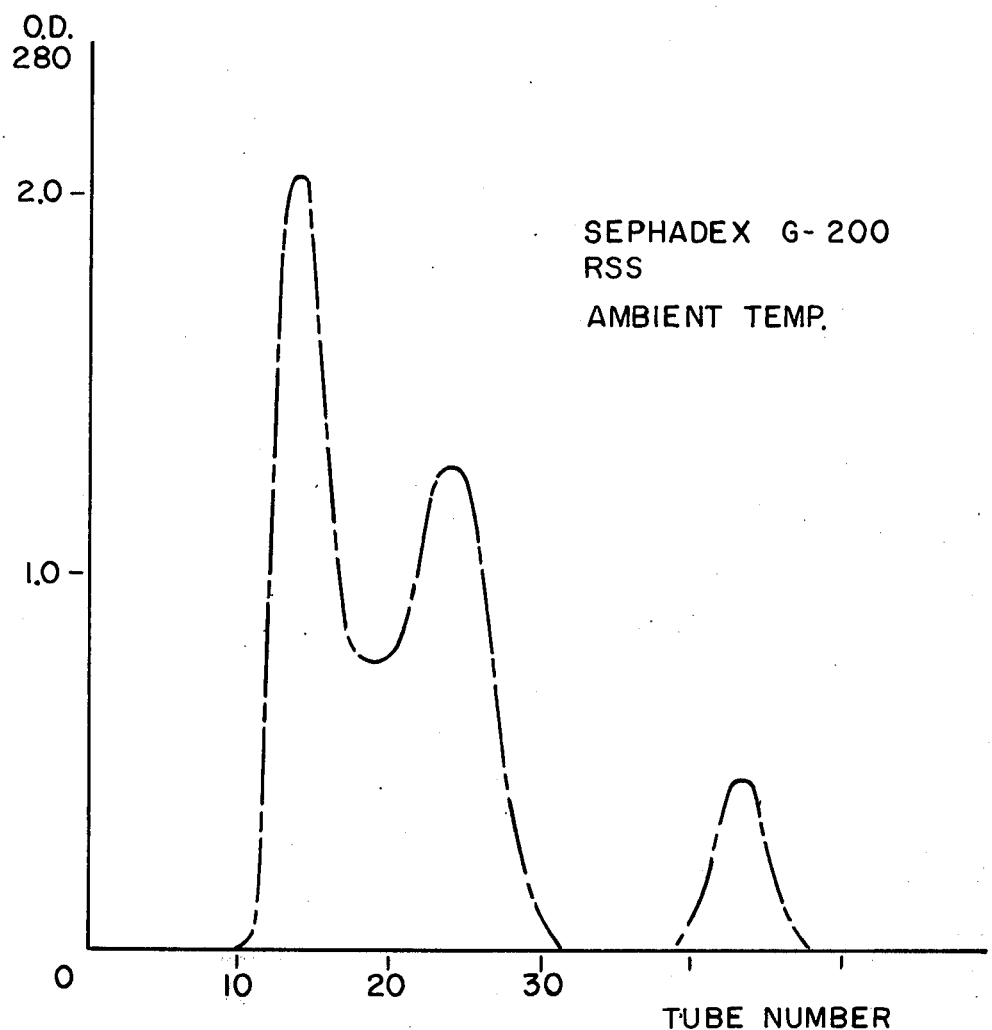

SNAKE VENOM INHIBITOR MATERIAL AND METHOD OF PURIFICATION

RELATED APPLICATIONS

This application is a continuation-in-part of U.S. patent application Ser. No. 399,469 filed Sept. 21, 1973, now abandoned, which is a continuation of application Ser. No. 239,327 filed Mar. 29, 1972 and now abandoned.

BACKGROUND OF THE INVENTION

It is known in the literature that useful products for inhibition of snake venom and certain proteolytic enzymes can be obtained from snake serum as for example described in U.S. Pat. Nos. 3,336,204 and 3,504,083. However, it has been difficult to obtain the active ingredients in such snake serum in a highly purified form devoid of materials which are themselves reactive with and destructive to the human body. Moreover, it has been a problem to obtain such inhibitors from snake serum in the forms which are highly active after separation procedures.

SUMMARY OF THE INVENTION

According to the invention, a snake extract such as snake serum is purified to obtain a highly active therapeutic agent. The therapeutic agent is a protein which has been degraded or broken down to eliminate its antigenic properties yet retain its desirable biological active functions. Extraneous parts of the protein materials are removed. The splitting of the protein material and removal of the antigenic portion can be carried out by a number of procedures.

In one procedure, a liquid snake extract is reacted with a strong acid or acid salt to form a precipitate. The precipitate is then removed and the supernatant fluid is then dialyzed to remove traces of the acid or salt whereby a liquid remains carrying a useful therapeutic agent having extremely high activity in relation to protein material. The acid acts to split the original protein molecule leaving the useful therapeutic agent of this invention. Preferably the snake serum is mixed with an acid and heated for a short period of time. The acid produces a strongly acid reaction. A precipitate forms which sinks to the bottom of the tube after centrifugation. The clear liquid at the top is removed and then placed in a dialysis bag and dialyzed with isotonic sodium chloride solution to obtain a clear supernatant liquid which contains a useful treating agent. The treating agent is at least 10 times as active as crude serum in relation to protein concentration. The material obtained is then used to inhibit snake venom proteases and toxicity by introduction into the body of man and animals. Preferably the snake serum is used in an amount of 2 volumes to 1 volume of for example 4.5 N hydrochloric acid.

In another method of obtaining the therapeutic agent of this invention, original snake serum or snake extract is treated with an enzyme such as trypsin, chymo trypsin, or papain to split the protein molecules and obtain the therapeutic agent of this invention. This can be done by first removing desired protein fractions in a fractionating column and then treating the protein fractions with enzymes or by contacting original snake serum with proteolytic enzymes to obtain the split protein materials which act as therapeutic agents of this invention.

It is a feature of this invention that snake serum or snake extract is detoxified preferably simultaneously with the acidification or enzyme treating step to obtain a purified treating agent which is useful as an inhibitor of snake venom proteases and snake venom toxicity in animals. The purified material can be used in the treatment of snake bite victims. The purified material can have a specific activity such that 16 times as active as presently used antivenin such as Weyth's antivenin. The purified material is found to be a protein or polypeptide which retains its activity after the purification steps of this invention and in fact is split with the final material comprising a fragment of the material originally present in the body. The therapeutically active portion of the material remains while portions of the original protein molecule which are antigenic to humans are removed by the process of this invention and split from the active sites.

It is an object of this invention to provide a purification method for obtaining a highly active inhibitor from snake serum which inhibitor is useful as an antivenin.

It is another object of this invention to provide a purified snake extract containing protein or polypeptide therapeutic agent having high inhibitor activity.

DESCRIPTION OF PREFERRED EMBODIMENTS

The snake extract to be purified by the method of this invention can be taken from any organic tissue or body fluid of the snake. When the organ tissues are used, they are ground to a liquified form which is used as the starting snake extract material.

Preferably, however, the starting extract is snake serum. Any snake serum is useful. For example, useful snake serums can be obtained from widely varying types of snakes including the Florida rattlesnake (Crotalus adamanteus), water moccasin (Agkistrodon piscivorus), Japanese habu (Agkistrodon Blomhoffi), king snake (Lampropeltis getulus), Japanese garter snake (Elaphe Quadrivirgata), Hog nose snake (Heterodon platyrhinos), Eastern racer snake (Coluber constrictor constrictor), Rat snake (Elaphe olsoleta spiloides), Common water snake (Natrix sipedon sipedon), Painted water snake (N. erythrogaster erythrogaster), Common garter snake (Thamnophis ordivatus), South American boa constrictor, Scarlet snake (Amorphora doliata) and Mud snake (Farancia abacura).

Preferably the serum is obtained by cutting off a portion of the snake's tail and allowing the blood to flow into a sterile container. The serum is separated from the cells by centrifugation in a conventional manner. Rattlesnake serum is preferred for use in this invention since it is most readily available in commercial quantities.

The serum or other extract used as a starting material can be frozen for long periods of time as for example 2 years or longer at 0° C while maintaining the therapeutic agent of this material such that when thawed, and treated in accordance with this invention, highly active inhibitors are obtained.

In a first specific method, a soluble acid or acid salt is used as described in parent U.S. application Ser. No. 239,327, now abandoned.

Broadly, the snake serum or other liquid snake extract is mixed with a soluble acid or acid salt in the range of from 0.05 to 10.0 Normal. Thus the pH of the solution mixture is preferably in the range of from pH 1 to 5 and most preferably pH 1–3. The acid can be added directly to the serum and dissolved therein or can preferably be added to the serum in the form of a concentrated solution such as an aqueous solution.

It is preferred that the mixture then be heated at a temperature in the range of from 35° to 75° C for from 5 to 45 minutes after which the mixture is centrifuged whereupon the precipitate sinks. The clear liquid remaining above the precipitate is then separated and treated to remove low molecular weight solids such as any remaining inorganic acid. For example, dialysis using 0.9% saline solution at temperatures of from 3° to 15° C can be used in this last separation procedure.

The remaining liquid is found to contain a therapeutic agent having high activity to inhibit snake venom and proteolytic enzymes of snake venom.

The acid acts by splitting the therapeutic material from the protein material in the original extract so that most of the inactive protein can in turn be precipitated by the acid ions present. Thus, the mixture with the acid or acid salt involves in effect an acidification of the snake extract.

Highly useful inorganic salts which permit purification without destroying the activity of the purified material (inhibitor) include, but are not limited to, ferric chloride, copper sulfate, ferric nitrate and ammonium oxalate. However, any inorganic salt which acts to precipitate protein without destroying the useful therapeutic material can be used.

In a first specific example of the acidification purification method of this invention, 2 cc of 4.5 N hydrochloric acid aqueous solution is mixed with 4 cc of rattlesnake serum resulting in a solution of rattlesnake serum which is 1.5 N. A precipitate forms. The mixture is then heated at 56° C for 15 minutes and is then centrifuged at 5,000 rpm for 10 minutes. The precipitate sinks to the bottom of the tube. The clear liquid supernate is then placed in a dialysis bag (membrane of conventional thickness) surrounded by isotonic sodium chloride buffered at pH 7.4 with 0.01M phosphate buffer at a refrigerator temperature of about 4° C.

Dialysis is continued for 8 hours with continuous stirring. The dialysis water of sodium chloride solution is 30 times the volume of material being dialyzed and is changed 3 times. At the end of 8 hours, the resultant material is removed from the dialysis bag and a clear supernatant liquid is obtained which is pH 7.2.

This supernatant purified liquid material contains the purified therapeutic agent of the present invention. Chemical tests by the Lowry technique reveal 300 mg% of protein. The purified material is of molecular weight 5,000 to 15,000 since it is non-dialyzable through the dialysis bag. The original volume of the serum-acid solution after dialysis is found to be 7 cc. Thus, the active therapeutic agent present in the original 4 cc of crude snake serum was diluted to 7 cc and notwithstanding this dilution, in vitro tests indicate an increase in inhibitor activity as shown in the following tests.

TEST I, GELATIN FILM TEST

Three series of doubling water dilutions of water moccasin venom are prepared in 0.1 cc volume in concentrations listed in Table I below. To each tube of the first series, 0.1 cc of physiological saline solution is added. To each tube of the second series, 0.1 cc of crude rattlesnake serum is added and to the third series, 0.1 cc of the purified liquid material of the example of this invention is added.

Strips of Kodak Verachrome black and white film are cut in a width of ¼ inch and placed in petri dishes. 0.02 cc of each of the above dilutions of moccasin venom is placed in the form of a droplet on the gelatin layer of the photographic film. The film strips are then incubated at 37° C for 1 hour and rinsed in gently flowing tap water. A plus reaction is recorded when the proteases of the snake venom have completely dissolved the gelatin exposing the transparent nitro-cellulose film. Endpoints of the various solutions are recorded in Table I.

TABLE I

NEUTRALIZATION OF WATER MOCCASIN VENOM PROTEASE BY THE PURIFIED MATERIAL OF THIS INVENTION AND BY CRUDE RATTLESNAKE SERUM
Readings after 1 hr. at 37° C

| | Initial dilutions of venom | | | | | | | | |
|---|---|---|---|---|---|---|---|---|---|
| | 100 | 200 | 400 | 800 | 1600 | 3200 | 6400 | 12800 | Saline |
| Saline | + | + | + | + | + | + | + | − | − |
| Crude Serum | + | + | − | − | − | − | − | − | − |
| Purified liquid material | + | + | − | − | − | − | − | − | − |

It can be seen from Table I that the purified material has at least the same activity as crude serum in inhibition of snake venom proteases. Since the purified material has only 300 mg% of protein in contrast to 3,300 mgms% protein in the crude serum there is, therefore, a 10-fold or greater increase in specific activity by this method of purification.

TEST II, NEUTRALIZATION OF LETHAL EFFECTS OF MOCCASIN VENOM BY PURIFIED LIQUID MATERIAL OF THIS INVENTION

A dosage of water moccasin venom at a level of 20 micrograms per gram of body weight is sufficient to kill 100% of mice so innoculated. 10 mice are innoculated with this dosage of water moccasin venom. Five of the mice had the venom mixed with saline only and the other five had the venom mixed with the purified liquid material of this invention at a dosage level of 0.06 cc per gram of body weight. It can be seen in Table II below that the five mice protected by the inhibitor of this invention survived whereas the five unprotected mice all died at the end of 24 hours. Thus, the purified inhibitor is an effective inhibitor of the toxicity of snake venom in mice.

TABLE II

NEUTRALIZATION OF LETHAL EFFECTS
OF WATER MOCCASIN VENOM IN MICE
BY PURIFIED LIQUID MATERIAL OF THIS INVENTION

| | No. Survived | No. Died |
|---|---|---|
| WMV + Saline | 0 | 5 |
| WMV + purified liquid material | 5 | 0 |

TABLE II-continued

NEUTRALIZATION OF LETHAL EFFECTS
OF WATER MOCCASIN VENOM IN MICE
BY PURIFIED LIQUID MATERIAL OF THIS INVENTION

| | No. Survived | No. Died |
|---|---|---|
| WMV — 20 mcg/gm Purified liquid material - .06 cc/gm | | |

While a first specific acidification example of producing a useful therapeutic agent by purifying a snake extract has been described, many variations are possible. For example, when ferric chloride, copper sulfate or ferric nitrate are used in Example I in place of the acid used, purification is obtained; however, the inhibitor has some loss of activity. When ammonium oxalate is substituted in Example I, a lower amount of purification of the inhibitor is obtained.

The times and temperatures used can vary greatly depending upon the specific inorganic salt or acid used. In all cases using the acid or enzyme procedures of this invention, a highly purified inhibitor is obtained from the snake extract by removal of inactive protein material leaving behind a highly active inhibitor with at least 10 times the specific activity of crude serum and many times the specific activity of commercial antivenins such as Weyth's antivenin. The inhibitor has use in the treatment of snake bite. The inhibitor is a protein or polypeptide substance which is non-toxic.

In the above method which is the first general method of this invention, snake serum is treated with a soluble acid or acid salt to reduce the pH of the serum to pH 1–5 and preferably 1–3, heated for from 35° to 75° C for from 5 to 45 minutes after which the precipitate is removed and dialysis used to remove the remaining inorganic acid and obtain a concentrated serum with a pH in the range of from preferably 7.0 to 7.6. Other methods to obtain the desired therapeutic agent of this invention are given below.

In a second method, snake serum or other snake extract is heat treated at the temperatures and times given with respect to the first method and the precipitate then removed. As a subsequent step, the pH is modified with an acid or acid salt to a pH of from 1 to 5 for a period of from 3 to 45 minutes at temperatures of from 35° to 75° C. A precipitate forms. The material is placed in a centrifuge for from 5 to 30 minutes at an rpm of from 2 to 5,000 forcing the precipitate to the bottom. The clear supernate is removed from the precipitate. This supernate is then dialyzed against 25 to 100 times its volume in 0.9% sodium chloride with 0.1 molar phosphate buffer at a pH range of from 7.0 to 7.6 leaving a final pH of 7.0 to 7.6 in the remaining material containing the treating agent of this invention.

In a third method, snake serum is treated in a fractionated column to remove protein fractions in the range of from 300,000 to 400,000 molecular weight. Test tubes are placed in a revolving drum underneath the column and the test tubes allow fluid from the column to drip from 1 to 15 minutes each with approximately 1 to 300 such tubes being used. The process of filtration lasts from 0.5 to 48 hours. The proteins of higher molecular weight come off first and those of smaller molecular weight come off last. The protein within the molecular weight range of from 10,000 to 90,000 are then split by treating the material in accordance with the first or second methods described above.

In a fourth method original snake serum is treated with a proteolytic enzyme at a pH in the range of from 7.4 to 7.0 for from 5 hours to 3 days preferably at a temperature in the range of from 25° to 37° C. The material is then fractionated to obtain the therapeutic agent of this invention.

In a fifth method, proteolytic enzymes are used as in the fourth method after first heat treating the serum at a temperature of from 45° C to 65° C for a time period of from 15 minutes to 60 minutes.

In a sixth method, which is a preferred method when using proteolytic enzymes to split the protein materials in snake serum, a fractionating column is used to obtain protein fractions in the range of from 10,000 to 90,000 molecular weight. Proteolytic enzymes are then used to split the protein materials to obtain the therapeutic agent of this invention while eliminating portions of the protein materials which are antigenic to man. The conditions of use are preferably as described in the fourth method.

Molecular sieving or serum fractionation is preferably used in conjunction with enzyme splitting to obtain the therapeutic agent of this invention from snake serum.

In a second specific example of this invention, 5 ml of rattlesnake serum is applied to a Sephadex G-200 column 3 × 90 cm. The column was obtained, prepared and conditioned as recommended by Pharmacia Fine Chemicals, Inc. of 800 Centennial Avenue, Piscataway, New Jersey. The column is essentially a standard column filled with Sephadex G-200 having a particle size of 40–120 microns. The column is used with upward flow adaptors and the molecular species are eluted with phosphate buffered saline (pH 7.4) at ambient temperature (25° C). The flow rate is adjusted to about 5 ml per 30 minutes and fractions are monitored by UV absorbance at 280 nm. A typical fractionating pattern is shown in FIG. 1. Within 10 to 15 ml of the void volume the first protein band appears as a sharp entity. The band contains molecular species above 200,000. The second protein band is incompletely separated from the first band. The median molecular weight of the proteins in the second band is about 160,000. A third distinct protein band elutes after 220 ml of buffer has passed through the column. The molecular weight of the proteins in this band is low and in the range of from 10 to 90,000. FIG. 1 illustrates the bands obtained.

A test procedure is set up to determine the effectiveness of the material obtained in Example II to inhibit the effects of water moccasin venom. In each case, 30 micrograms of water moccasin venom per gram of mice body weight was injected IP. Table X below shows, inter alia, that when 0.2 mg per gram of body weight of the second protein band is injected IP into a mouse injected with 30 micrograms of water moccasin venom IP, 100% survival is obtained after a 3 hour period.

TABLE X

Mortality Test

| Groups of Mice (wt. 10–14 gm each injected with 30 mg venom/gm of mouse weight) | | Dead/Alive (after 3 hours) |
|---|---|---|
| Unprotected | | 4/5 |
| Rattlesnake serum | 0.2 mg/gm of mouse weight | 0/6 |
| Protein band 1 | 0.2 mg/gm of mouse weight | 4/5 |
| Protein band 2 | 0.2 mg/gm of mouse weight | 0/6 |

Protein band 2 contains a venom inhibiting factor. However, protein band 2 is preferably treated by a method of this invention to highly concentrate the therapeutic agent of this invention by splitting antigenic protein protions of the molecule therefrom. Thus, in a third example, the second protein band from the Sephadex G-200 column was exposed to "Enzite-Try" at a rate of 10 milligrams per 5 milligrams of band 2 at 37° C for 16 hours to enable the trypsin to digest the protein fraction. Enzite-Try is a trademarked product of Sigma Chemical Co. of St. Louis, Missouri having trypsin as its active ingredient. The trypsin treatment hydrolyzes peptide bonds. The trypsin is removed after 16 hours by centrifugation at 2000 rpm for 15 minutes and ambient temperature (25° C). The therapeutic agent of this invention which inhibits the harmful effects of snake venom, and has a molecular weight of from 10,000 to 45,000 is found to be present. This therapeutic agent when injected into mice at the levels as indicated in Table Y is found to be fully protective at low levels of injection. This illustrates the concentration of therapeutic agent by treatment with the enzyme method of this invention.

TABLE Y

| Mortality Test Groups of Mice (wt. 10–14 gm each injected with 30 mg venom/gm of mouse weight | Dead/Alive (after 3 hours) |
|---|---|
| Unprotected | 5/5 |
| ENZ-TRY Band 0.074 mg/gm of mouse weight | 0/5 |
| ENZ-TRY Band 0.037 mg/gm of mouse weight | 3/5 |

The present invention results in obtaining an inhibitor agent which is a protein fraction having a molecular weight of from 10,000 to 45,000 and which is capable of neutralizing the lethal effects of snake venom in animals. This fraction is obtained from crude protein fractions in crude snake serum which have molecular weights of up to 200,000 or 300,000 which are concentrated fourfold to have high activity by splitting or digestion so as to have molecular weights of from 10,000 to 45,000. This fraction has active sites which survive treatment by strong acids and proteolytic enzymes. The specific activity of the inhibitor resulting from the methods of this invention is considerably greater than that of untreated snake serum. Moreover, when compared with a commercially sold antivenin such as Crotalidae produced by Wyeth Laboratories, Inc. of Marietta, Pennsylvania, the antivenin of this invention has 16 times the specific activity thereof. In a comparative test on live mice, only 0.07 mg/gm of mouse body weight of the therapeutic agent obtained in the third example is needed to keep alive 5 mice injected with 30 mg rattlesnake venom/gm of mouse body weight whereas 1.2 mg/gm of mouse body weight of Crotalidae was found to produce the same result.

What is claimed is:

1. A method of purifying snake blood serum to obtain an inhibitor of snake venom, said method consisting essentially of,
    forming a precipitate in snake blood serum by reacting said serum, at a pH below about pH 3, with a quantity of a strong acid or inorganic salt pH lowering material reactive with protein material contained in said extract in an amount sufficient to form a precipitate,
    removing said precipitate from the thus treated serum,
    and removing traces of said pH lowering material that may remain in the supernatant liquid to obtain a liquid substantially free of antigenic protein material.
2. A method in accordance with the method of claim 1 wherein said pH lowering material is removed by dialysis.
3. A method in accordance with the method of claim 2 wherein said pH lowering material is selected from the group consisting of hydrochloric acid, ferric chloride, copper sulfate, ferric nitrate and ammonium oxalate.
4. A method in accordance with the method of claim 2 wherein said acid is hydrochloric acid and said snake serum is dissolved in said acid at a range of 0.05 to 10.0 Normal.
5. A method in accordance with the method of claim 4 wherein said precipitate is formed in said snake serum by allowing said reaction to proceed at a temperature in the range of from 35° C to 80° C for from 5 to 50 minutes.
6. The method of claim 1 wherein said reacting is carried out in the range of from pH 1 to pH 3.
7. A method of purifying snake blood serum to obtain an inhibitor of snake venom, the method consisting essentially of:
    treating snake blood serum with a proteolytic enzyme to split the protein portion of the serum from the remaining portions thereof;
    selectively fractionating and removing the higher molecular weight protein portions from the serum;
    isolating and recovering the lower molecular weight portions of the serum to obtain a liquid substantially free of antigenic protein material, thereby producing a concentrated snake venom inhibitor the active portion thereof having a molecular weight of from about 10,000 to about 45,000.
8. The product produced by the method of claim 7.

* * * * *